US009228958B2

(12) United States Patent
Shirkhodaie et al.

(10) Patent No.: US 9,228,958 B2
(45) Date of Patent: Jan. 5, 2016

(54) PROTOCOL-BASED INSPECTION SYSTEM (75) Inventors: Amir Shirkhodaie, Nashville, TN (US);
Robert Moriarty, Greenwood, IN (US);
Kong Ma, Carmel, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 972 days.

(21) Appl. No.: 13/416,610

(22) Filed: Mar. 9, 2012

(65) Prior Publication Data

US 2012/0229619 A1    Sep. 13, 2012

Related U.S. Application Data (60) Provisional application No. 61/451,035, filed on Mar. 9, 2011.

(51) Int. Cl.
*G06T 7/00* (2006.01)
*G01N 21/89* (2006.01)

(52) U.S. Cl.
CPC .......... *G01N 21/8901* (2013.01); *G06T 7/0004* (2013.01); *G06T 2200/24* (2013.01); *G06T 2207/20081* (2013.01)

(58) Field of Classification Search
CPC ............ G06T 2207/30164; G06T 2207/30108
USPC .......................................................... 348/92
See application file for complete search history.

(56) References Cited

U.S. PATENT DOCUMENTS

| | | |
|---|---|---|
| 5,149,978 A | 9/1992 | Opsal et al. |
| 5,615,003 A | 3/1997 | Hermary et al. |
| 5,815,198 A | 9/1998 | Vachtsevanos et al. |
| 5,962,853 A | 10/1999 | Huth-Fehre et al. |
| 6,229,872 B1 | 5/2001 | Amos |
| 6,290,784 B1 | 9/2001 | Yasuhara et al. |
| 6,526,008 B1 | 2/2003 | Caponetto et al. |
| 6,703,633 B2 | 3/2004 | Tullis |
| 7,397,550 B2 | 7/2008 | Hackney et al. |
| 8,222,126 B2 | 7/2012 | Tanaka et al. |
| 8,349,080 B1 | 1/2013 | Price |
| 8,398,725 B2 | 3/2013 | Tanaka et al. |

(Continued)

FOREIGN PATENT DOCUMENTS

EP    1017044 A1    7/2000

OTHER PUBLICATIONS

International Search and Written Opinion, ISA/US, PCT/US2012/028509, Rolls-Royce Corporation, May 23, 2012.

*Primary Examiner* — Sath V Perungavoor
*Assistant Examiner* — Jeffery Williams
(74) *Attorney, Agent, or Firm* — Shumaker & Sieffert. P.A.

(57) ABSTRACT

One form of the present application provides a system comprising an illumination source capable of providing an electromagnetic illumination of an engine component, an imaging system structured to capture illumination of the engine component, a component manipulation system structured to position the engine component in a variety of orientations relative to one of the illumination source and the imaging system, a computer based user interface capable of identifying an inspection protocol defined to acquire an image of the engine component at the variety of positions using the illumination system, the imaging system and the component manipulation system, and a processor configured to process the inspection protocol for the purposes of analyzing the acquired image in response to the inspection protocol.

14 Claims, 5 Drawing Sheets

(56) References Cited

U.S. PATENT DOCUMENTS

| | | |
|---|---|---|
| 2002/0054694 A1 | 5/2002 | Vachtsevanos et al. |
| 2002/0128790 A1 | 9/2002 | Woodmansee |
| 2002/0159560 A1 | 10/2002 | Nienaber et al. |
| 2003/0016856 A1 | 1/2003 | Walker et al. |
| 2003/0038932 A1 | 2/2003 | Wienecke et al. |
| 2004/0083024 A1 | 4/2004 | Wang |
| 2005/0036135 A1 | 2/2005 | Earthman et al. |
| 2005/0201611 A1 | 9/2005 | Lloyd, Jr. et al. |
| 2006/0078193 A1 | 4/2006 | Brummel et al. |
| 2007/0217672 A1* | 9/2007 | Shannon et al. ............... 382/152 |
| 2008/0044069 A1* | 2/2008 | DuGal .......................... 382/128 |
| 2008/0151262 A1 | 6/2008 | Tanaka et al. |
| 2008/0282972 A1 | 11/2008 | D'Souza et al. |
| 2009/0033947 A1 | 2/2009 | Boyer et al. |
| 2009/0066939 A1 | 3/2009 | Venkatachalam et al. |
| 2009/0279772 A1* | 11/2009 | Sun et al. ..................... 382/141 |
| 2010/0100275 A1* | 4/2010 | Mian et al. ..................... 701/29 |
| 2010/0172567 A1 | 7/2010 | Prokoski |
| 2010/0207040 A1 | 8/2010 | Tanaka et al. |

* cited by examiner

PROTOCOL-BASED INSPECTION SYSTEM

CROSS REFERENCE TO RELATED APPLICATIONS

The present application claims the benefit of U.S. Provisional Patent Application 61/451,035, filed Mar. 9, 2011, and is incorporated herein by reference. This application also incorporates by reference, in their entirety, the following concurrently filed applications: INTELLIGENT AIRFOIL COMPONENT SURFACE IMAGING INSPECTION, U.S. patent application Ser. No. 13/416,315; INTELLIGENT AIRFOIL COMPONENT GRAIN DEFECT INSPECTION, U.S. patent application Ser. No. 13/416,516; INTELLIGENT AIRFOIL COMPONENT SURFACE INSPECTION, U.S. patent application Ser. No. 13/416,409; AUTOMATED OBJECT MANIPULATION SYSTEM, U.S. patent application Ser. No. 13/416,409; and ILLUMINATION SYSTEM WITH ILLUMINATION SHIELD, U.S. patent application Ser. No. 13/416,770.

TECHNICAL FIELD

The present invention generally relates to inspection systems, and more particularly, but not exclusively, to a protocol-based inspection system.

BACKGROUND

Present approaches to inspection systems suffer from a variety of drawbacks, limitations, disadvantages and problems including those respecting repeatability, adaptability and others. There is a need for the unique and inventive protocol-based surface inspection apparatuses, systems and methods disclosed herein.

SUMMARY

One embodiment of the present invention is a unique protocol-based inspection system. Other embodiments include apparatuses, systems, devices, hardware, methods, and combinations for a protocol-based inspection. Further embodiments, forms, features, aspects, benefits, and advantages of the present application shall become apparent from the description and figures provided herewith.

DETAILED DESCRIPTION OF THE ILLUSTRATIVE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1:
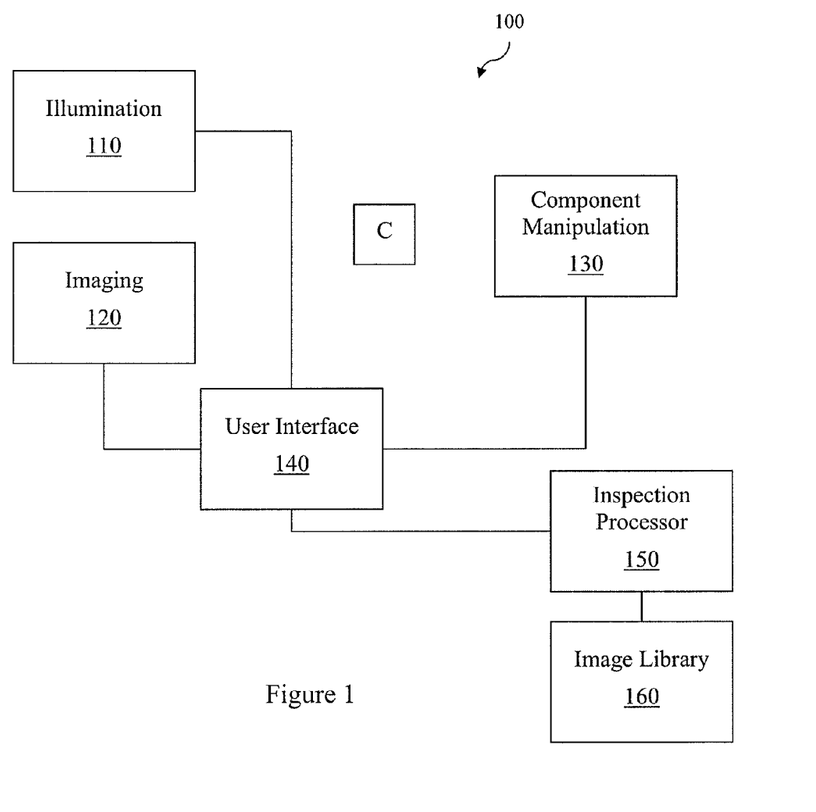
FIG. 1 is a schematic of an embodiment of an inspection system of the present application.

With respect to FIG. 1, an embodiment of an intelligent automated visual inspection system 100 is disclosed which is capable of acquiring and processing images of components such as, but not limited to, engine components such as airfoils of gas turbine assemblies. The embodiment of inspection system 100 as shown in FIG. 1 includes an illumination system 110, an imaging system 120, a manipulation system 130, a user interface 140, an inspection processor 150, and an image library 160.

An illumination system such as system 110 can include a source of radiance to be directed toward a component C under inspection. The radiance can be reflected by the surface of component C and detected by imaging system 120. Radiance type can include various wavelengths in the electromagnetic spectrum including but not limited to the visible spectrum, ultraviolet light, near infrared, and x-rays. The source of radiance can include a laser, a discharge tube and the like. In one embodiment, an imaging system can be a camera utilizing a conventional light or other electromagnetic radiation type such as x-ray, ultraviolet, fluorescent and the like. An embodiment of manipulation system 130 can include a robotic part manipulator and positioning algorithms to provide predetermined part presentation and positioning during an inspection process.

User interface 140 includes an interface having parameters within modules to be selected by a user in determining a set of inspection protocols. The inspection protocols can provide control of illumination system 110, imaging system 120 and manipulation system 130 to produce an acquired image of component C under inspection. The acquired image can be analyzed by inspection processor 150. The inspection protocols can further be applied to the analysis of the acquired image. In another embodiment, the analysis includes referencing image library 160.

Inspection system 100 can be used to analyze and determine characteristics or manufacturing flaws in components being inspected. In one embodiment, inspection system 100 is a protocol-based visual inspection system with image processing algorithms and techniques implemented in system software. A system of such an embodiment can offer intuitive and easy-to-use interfaces to develop visual inspection procedures of components. In some forms, inspection system 100 can be used without writing lines of programming code. An inspection system of another embodiment of the present application is fully automated, adaptive, and customizable to perform complex visual inspection comparable to that of a human inspector. The protocol-based system of yet another embodiment can have a built-in capability to simultaneously facilitate automated control of the visual inspection system including the accompanying illumination, imaging, and component manipulation systems.

An inspection system of one embodiment can have a protocol-based development technique which follows an interactive process. Through a process such as the one found in this embodiment of the present application, inspectors can fine tune the inspection system control parameters to achieve the inspection of components to various degrees of requirements, yet within an acceptable margin recommended by the Engineering Inspection Standards (EIS) among other potential standards, targets, goods, etc. The system protocols of this embodiment can have built-in memory where detected component features or flaws can be registered as a historical representation of previously detected manufacturing imperfections. As such, a component designer can view a surface map of previously encountered manufacturing features, trouble shoot the cause of the features and revise the design and/or the manufacturing processes which potentially may be causing such component imperfections.

Figure 2:
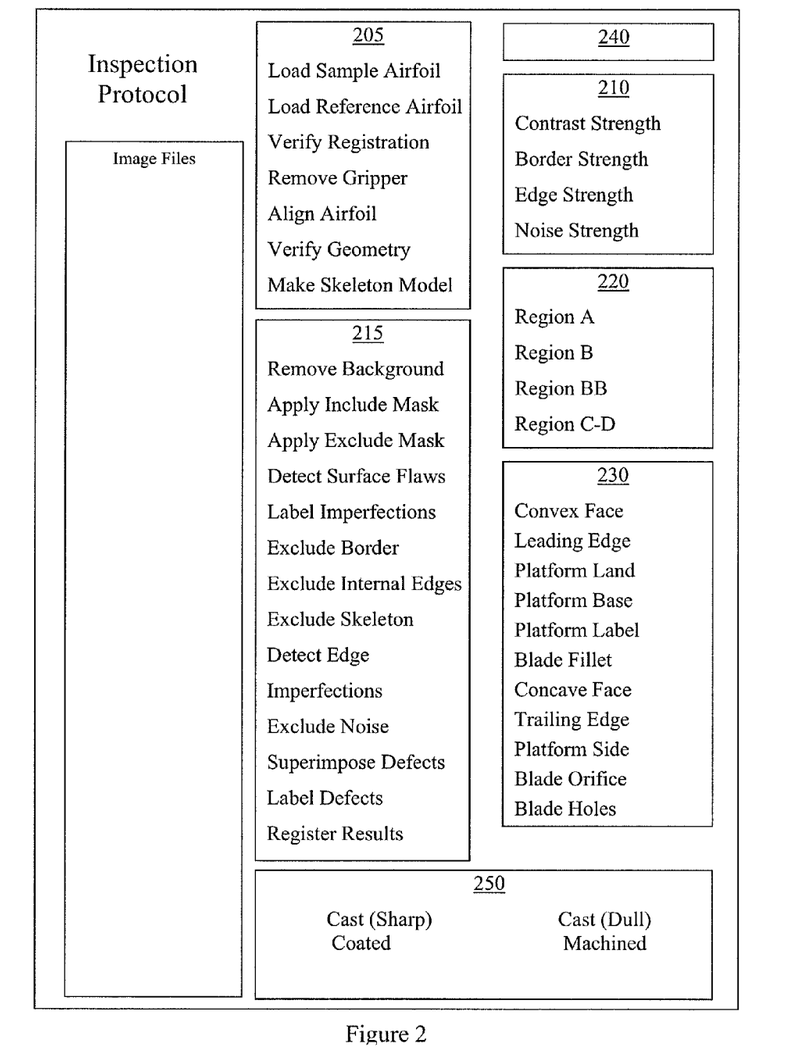
FIG. 2 is an illustration of a graphical user interface of an embodiment of an inspection system of the present application.

With respect to FIG. 2, one embodiment of an inspection system's graphical user interface (GUI) for development of inspection protocols is illustrated. The description that follows is an example of a manner of interacting with a GUI and configuring and/or executing an inspection protocol. It will be appreciated that any number of variations in the GUI, in protocol development and execution, etc. are contemplated herein. Furthermore, additional or fewer GUI options, combinations of features used in the GUI, etc, than those described herein are contemplated.

In some forms, code programming is not required for development of the protocols. In one embodiment, an inspection protocol is interactively designed to meet a selected inspection requirement with inspection protocol development tools selected in an inspection protocol module 215. A user designs a protocol by selecting a series of available inspection options in an inspection setup requirement module 205 and by defining four inspection parameters in an inspection process control parameters module 210 including: contrast strength, border strength, edge strength, and noise strength. In one embodiment, an inspection protocol is interactively designed to meet a selected inspection requirement with inspection protocol development tools selected in an inspection protocol module 215. In a further embodiment, an inspection of a component can consist of individual protocols to be executed during the inspection process one by one in the order they are constructed.

As demonstrated in FIG. 2, an exemplary inspection system in one embodiment can further allow the user to select inspection regions of components with a designated component regions module 220 consistent with the specified EIS requirements in an EIS specification requirements module 240. In a further embodiment, per protocol, the user can specify the section of a component to be inspected in a component section inspection module 230 according to component linguistic terminology. The exemplary inspection system protocol development GUI shown in FIG. 2 can allow the user to specify surface conditions of components being inspected with an intrinsic surface conditions module 250. A still further embodiment can allow the user to control parameters enabling synchronization of inspection sub-components including, but not limited to, illumination, imaging, and component manipulation systems. For example, the embodiments of the inspection systems and associated systems described herein can be used to control the illumination system, camera parameters, and component manipulators together, either concurrently or in a controlled sequence, with minimal to no additional interaction from an operator.

Figure 3:
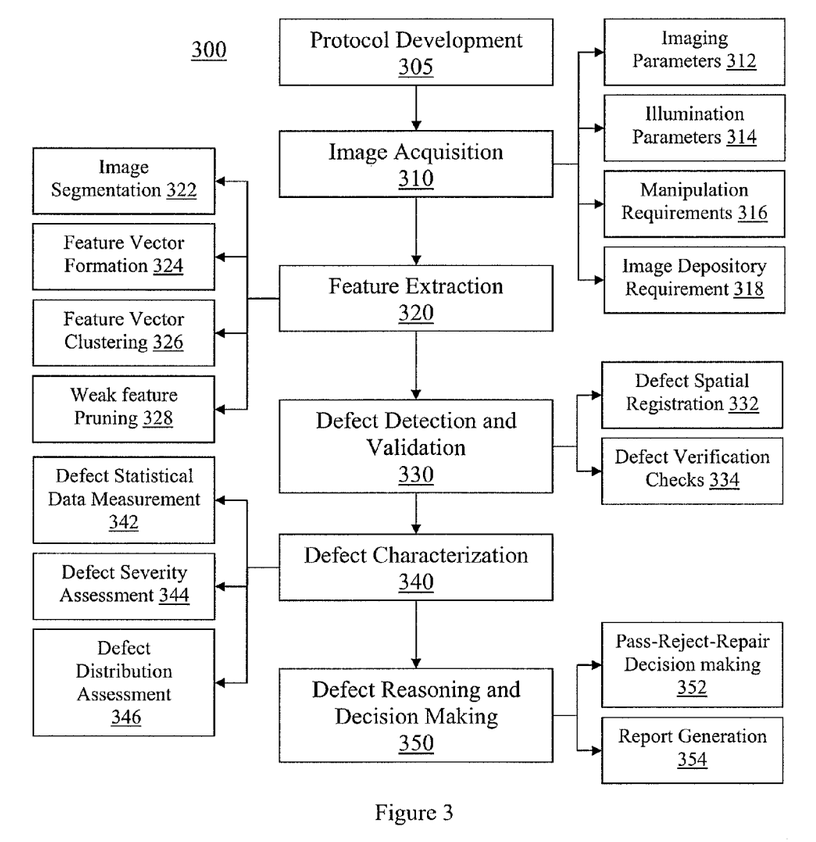
FIG. 3 is a process flow diagram of an embodiment of an inspection process of the present application.

FIG. 3 illustrates a flow chart representing steps for an automated inspection process 300 that can be done through an embodiment of a GUI, for example an embodiment that is disclosed herein. Inspection process 300 is shown as initiating with operation 305 which develops the inspection protocol. A designed inspection protocol of one embodiment can control the illumination system, the imaging parameters, and the component manipulation system in response to the inspection protocol. Built-in communication capabilities of an inspection system of an embodiment of the present application can facilitate synchronization of inspection hardware and software.

Following operation 305 is operation 310 which is an image acquisition operation accessing an imaging parameters module 312, an illumination parameters module 314, a component manipulation requirements module 316 and an image depository requirement module 318. An imaging system operating under imaging parameters module 312 can be a camera utilizing a conventional light or other electromagnetic radiation type such as x-ray, ultraviolet, fluorescent and the like. Illumination parameters module 314 can correspond with the technology of imaging parameters module 312. Component manipulation requirements module 316 can include manual, automated, or semi-automated instructions and controls to manipulate a component during inspection. In a specific embodiment, automated component manipulation controls can be determined in response to a component identification process. The identification process can be integrated with image depository requirement module 318.

Upon acquisition of the component image, inspection process 300 performs steps to segment the background from the foreground and component in operation 320 shown as following operation 310. Operation 320 is a feature extraction process including an image segmentation module 322, a feature vector formation module 324, a feature vector clustering module 326 and a weak feature pruning module 328. Separately or in combination, modules 322, 324, 326 and 328 of feature extraction operation 320 can identify and remove segments of the component image acquired in operation 310 deemed unnecessary or periphery. In various embodiments, removal of these segments allows an image with sharper edges for edge detection analysis or smooth shading for defect detection analysis, for example. Once segmented in feature extraction of operation 320, the image background information can be ignored.

In yet a further embodiment, the ability to include and exclude certain features of the component C can also be provided. For example, the GUI described above can include, or alternative take the form of, a mask construction GUI that permits an operator to mask a specific region of the component C. A polygon mask can be used in some forms and can have any geometrical shape useful to identify certain areas of the component C. The GUI can also permit an operator to import and export masks associated with an inspection protocol. The features available to the operator can permit the mask to be translated, rotated, expanded, shrunk, etc to identify certain areas. In some forms one or more vertices of a polygon mask can be manipulated through the GUI. Two types of masks can be used in the various embodiments of the system described herein. An "Include Mask" and an "Exclude Mask" can be used. The Include Mask can enclose a section of the component C that is subjected to inspection, while the Exclude Mack can define sections of the component C that should be excluded from inspection. In some forms one Include Mask and one Exclude mask are permitted for any given protocol.

Upon segmentation of the foreground including the component subject to inspection from the background, defective regions can be determined in defect detection and validation operation 330. Defects can include burrs, nicks, marks, scores, pitting, dents, and visible cracks to name a few. Operation 330 includes a defect spatial registration module 332 and a defect verification checks module 334. Defect spatial registration module 332 can, for example, in one embodiment provide location information of a determined defect by coordinating with a component manipulation system. The spatial information can be used to communicate the location of the detected defect to a user. Defect verification checks module 334 can operate to provide information regarding characterization of a defect such as, but not limited to, the severity and type of defect detected. Defect verification checks module 334 can provide this characterization information to the next operation.

Operation 340 is shown following operation 330 and is a defect characterization operation including quantitative and qualitative analysis. Operation 340 applies a defect statistical data measurement module 342 to define geometrical properties of an identified defective area. In one embodiment, fuzzy logic analysis can be applied in one or more portions of the inspection process 300. The qualitative judgment can provide an indication of the acceptability of a component with a defect according to the inspection standards being applied. Furthermore, each defective area can be characterized based on both quantitative and qualitative measures with the application of a defect severity assessment module 344 and a defect distribution assessment module 346. Severity and distribution assessment can provide information relevant to determining a cause for the detected defects in addition to contributing to decisions regarding acceptability of a component.

In operation 350, defect reasoning and decision making, inspection process 300 can use an analysis technique to perform defect condition reasoning with respect to the inspection engineering standards and an image library. Fuzzy logic analysis can be applied in operation 350. With the assessment of operation 350, a recommendation can be made for passing, recalling, or rejecting the inspected component in decision making module 352 and a report can be generated in report generation module 354.

Figure 4:
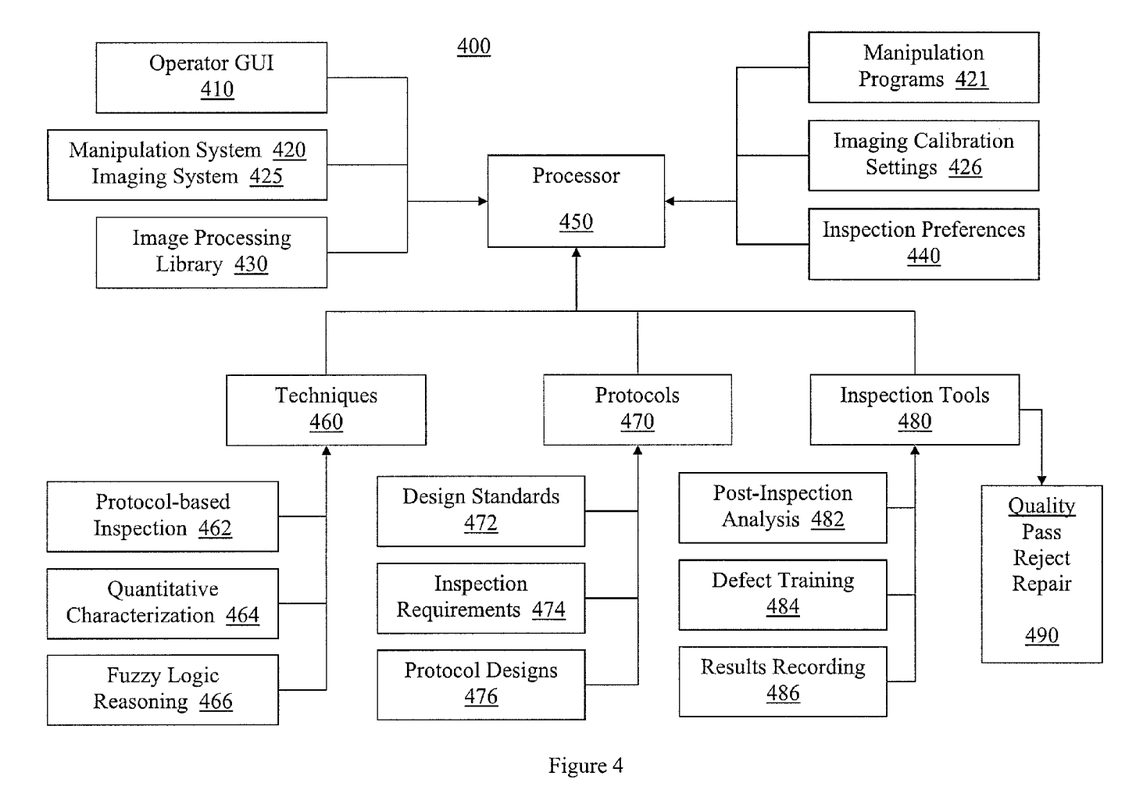
FIG. 4 is a schematic diagram of an embodiment of a component of an inspection system.

FIG. 4 illustrates an embodiment of functional components with an inspection processor 450 of an inspection system 400. Inspection processor 450 is represented as a single component containing hardware capable of performing various functions. Each function can be located on a separate piece of hardware and can be one of several hardware varieties available and arranged by one skilled in the art. Processor 450 can also include one or more microprocessors where in one embodiment a single microprocessor can provide the function of each module or separate microprocessors can be used for one or more of the modules.

Functional components can include a graphical user interface 410, a component manipulation system interface 420, an imaging system interface 425, an image processing library 430 and an inspection preference interface 440. In various embodiments, image processing library is capable of providing images for identification, verification and assessment of images acquired from a component under inspection. Further, image processing library is capable of storing acquired images for application in subsequent image analysis. In one embodiment, component manipulation system interface 420 provides a communication interface to a manipulation system. In some forms the system 420 can be used to pass information from a manipulation programs module 421 when positioning a component. Manipulation programs module 421 can provide instructions for manipulating a component during an inspection process. Manipulation programs module 421 can also assess an object to determine the instructions to be applied when manipulating the component.

Imaging system interface 425 provides a communication interface to a imaging system. In some forms the system 425 can be used to pass information from an image calibration settings module 426 when acquiring an image of the component. Image calibration settings module 426 can provide assessment and control of the imaging system to ensure consistent performance. In one form, component manipulation system interface 420 can be a communication interface. In an alternative and/or additional form, imaging system interface 425 can be a communication interface.

In the embodiment shown in FIG. 4, inspection processor 450 is shown with a technique module 460, a protocol module 470 and an inspection tool module 480. Technique module 460 can include protocol based inspection 462, quantitative characterization 464, and fuzzy logic qualitative reasoning 466. These techniques can be applied during image analysis. Protocol module 470 can include design standards 472, inspection requirements 474, and protocol designs 476 selected with a user interface to provide parameters for the inspection process. Inspection tool module 480 can include post-inspection analysis 482, defect training 484, and results recording 486. Module 480 can operate in coordination with image processing library 430 to store products of inspection tool module 480. Inspection system 400 can also provide a component quality report 490 with status such as pass, reject, repair and recall, for example.

In another embodiment, an inspection system of one embodiment includes a defect training module. The inspection system supports an interactive process by which an inspector can train the inspection system to detect certain defect conditions. In one particular embodiment, the inspector can train the system with two different types of defects including Positive and Negative defects. Each defect category can be associated with a relative scaling factor of low, medium or large on a qualitative basis. Furthermore, the training can be used to specify the identified defect either as a "pass", a "reject", or a "rework" defective class. The system can maintain a library of inspection information such as a surface defect database. In one form, the library can contain hundreds of different surface conditions. The inspection library can be referenced when performing calculated assessments and intelligent reasoning about the condition of observed defects.

In yet another embodiment, an inspection system can support utilities for registering and displaying complete airfoil surface defect maps. The exemplary system can allow an inspector to view a substantially 360 degree surface defect map of inspected airfoil models. The inspection system can register and maintain spatial locations of defects in a traceable quad-tree format. The inspection system can also be capable of displaying historical inspection occurrence maps to allow the inspector to correlate defects with other input factors such as design and manufacturing parameters.

Figure 5:
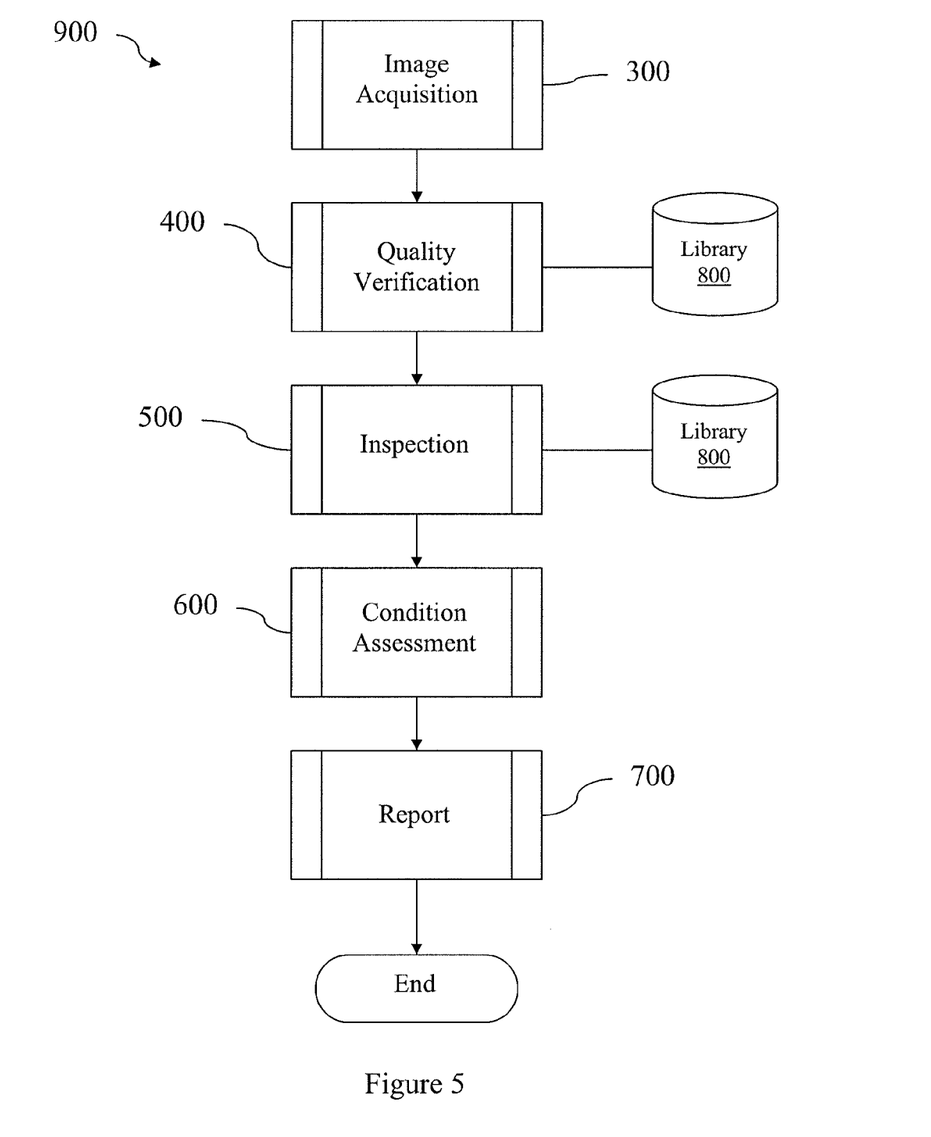
FIG. 5 is a process flow diagram of embodiment software of an inspection system of the present application.

FIG. 5 illustrates a process flow chart of one embodiment of the system software of an inspection process 900. Inspection process 900 as shown includes image acquisition 300 and quality verification 400 with comparison to a library of images 800 for inspection. In one embodiment, quality verification 400 can include modifying the image acquired to provide an image with edge strength for example. In another example, illumination can be adjusted to produce a specified image quality or the image can be segmented and background images can be removed. Image inspection 500 can provide an indication whether a component under inspection includes anomalies and irregularities in reference to images from library of images 800. In condition assessment 600, analysis of negative and positive imperfection and anomaly detections can be conducted using various techniques including model based, cognitive characterization and fuzzy logic. A report generator 700 can produce a report regarding the results of the various analysis techniques which can be made available to indicate component quality acceptability.

One aspect of the present application is a system including an illumination system; an imaging system; a manipulation system; a user interface capable of providing a set of inspection protocols for acquiring an acquired image with the illumination system, the imaging system and the manipulation system; an image library; and a processor capable of analyzing the acquired image in response to the set of inspection protocols and the image library where the set of inspection protocols can be capable of operating simultaneously to facilitate automated control of at least one of the illumination system, the imaging system, and the manipulation system.

Features of this aspect include the manipulation system being further capable of applying a predetermined manipulation program in response to the acquired image; the imaging system further having a set of camera calibrations for acquiring the acquired image and storing a set of analysis results from the analysis of the acquired image; the processor being further capable of evaluating the acquired image to identify a component being analyzed and identifying at least one segment of the acquired image, determining a feature strength of the at least one segment, and modifying the at least one segment of the acquired image in response to the feature strength; and the processor being structured to further include a technique module, a protocol module, and an inspection module.

Another aspect of this application is a method including the steps of developing a inspection protocol with a graphical user interface; allowing synchronization of a set of analysis operations in response to the inspection protocol; acquiring a component image of at least a portion of a component; extracting at least one image feature from the component image; characterizing a surface feature from the component image; and determining a quality assessment in response to characterizing the surface feature. Features of this aspect can include generating a report in response to the quality assessment; generating a historical representation of the surface feature; determining a cause for the surface feature; and modifying at least one of a set of design parameters and a set of manufacturing process parameters in response to the cause for the surface feature.

Further features can include developing the inspection protocol by selecting a series of available inspection options and defining a set of inspection parameters including at least one of contrast strength, border strength, edge strength, and noise strength; allowing synchronization of the set of analysis operations with an illumination operation, a manipulation operation and a detection operation; acquiring the component image by applying an illumination operation, a manipulation operation, and a detection operation to the component and applying a storage operation to the component image and specifying an inspection region of the component; determining the manipulation operation of the component in response to acquiring the component image; characterizing the surface feature by applying a statistical data measurement, a defect severity assessment and a defect distribution assessment and applying a fuzzy logic analysis; determining the quality assessment further includes selecting at least one of a pass grade, a reject grade, and a repair grade.

Yet another aspect of the present application provides a system comprising an illumination source capable of providing an electromagnetic illumination of an engine component, an imaging system structured to capture illumination of the engine component, a component manipulation system structured to position the engine component in a variety of orientations relative to one of the illumination source and the imaging system, a computer based user interface capable of identifying an inspection protocol defined to acquire an image of the engine component at the variety of positions using the illumination system, the imaging system and the component manipulation system, and a processor configured to process the inspection protocol for the purposes of analyzing the acquired image in response to the inspection protocol.

Further features include wherein the user interface is configured to provide a plurality of inspection protocol attributes capable of being selected by an operator; wherein the plurality of inspection protocol attributes includes one of image settings, lighting settings, and component features; wherein the plurality of inspection protocol attributes includes a masking feature to be applied to the acquired image; wherein the user interface permits a selection of a predefined inspection protocol; wherein the user interface is capable of building an inspection protocol that can be saved and re-used at a later inspection activity; an image library that can be referenced as a result of an inspection protocol, the image library providing a reference for determination of component inspection; wherein the processor is capable of performing fuzzy analysis instructions to assess a defect in the engine component; and wherein the set of inspection protocols is further capable of being synchronized to facilitate automated control of at least one of the illumination source, the imaging system, and the component manipulation system.

Still yet another aspect of the present application provides a method comprising developing an inspection protocol of an article of inspection with a graphical user interface, the developing including: setting an image parameter including one of contrast, brightness, and noise, selecting a protocol option including one of removing a background, labeling a flaw, detecting an edge, and applying a mask, identifying a location of the component to be evaluated, as a result of the developing, launching the inspection protocol, and synchronizing a component illumination, image acquisition, and a component manipulation in operative communication with a processor that receives information from the developing.

Still further features of the present application provide wherein the developing is the result of loading an inspection protocol from a predefined protocol, wherein the developing includes repeating the developing after the synchronizing prior to storing the inspection protocol. Other features further include evaluating a data produced from an inspection after the synchronizing. Still other features of the present application provide wherein the evaluating includes conducting a fuzzy logic analysis to produce an output, wherein the developing further includes applying a mask to an image provided by the image acquisition. Yet further features includes generating a report that describes the result of the inspection. Still other features further include determining at least one of a pass grade, a reject grade, and a repair grade prior to the generating. Still other features further include interfacing with a historical library and comparing an inspection conclusion of pass/fail as a result of the synchronizing with the historical library. Still another feature includes wherein the component manipulation includes placing the article of inspection in a variety of positions in which an image is acquired of the article of inspection.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A system comprising:
an illumination source configured to illuminate an engine component using visible light;
an imaging system configured to capture a surface image of the engine component based on the illumination of the engine component using the visible light;
a component manipulation system configured to position the engine component in a variety of orientations relative to at least one of the illumination source and the imaging system; and
a computer based user interface comprising an inspection processor, wherein the computer based user interface is configured to allow a user to select an automated inspection protocol, and wherein the inspection processor is configured to perform the automated inspection protocol to:
acquire surface images of the engine component at the variety of positions using the illumination system, the imaging system, and the component manipulation system,
perform a fuzzy logic analysis on at least one of the surface images of the engine component to detect a defect on a surface of the engine component, and
report the defect to the computer based user interface.

2. The system of claim 1, wherein the computer based user interface is further configured to allow the user to select a plurality of inspection parameters, wherein the plurality of inspection parameters includes at least one of a contrast strength, a border strength, an edge strength, or a noise strength.

3. The system of claim 2, wherein the plurality of inspection parameters includes a masking feature applied to a surface image of the engine component.

4. The system of claim 1, wherein the computer based user interface is configured to allow the user to select a plurality of automated inspection protocols.

5. The system of claim 2, wherein the computer based user interface is further configured to allow the user to develop an inspection protocol based on at least one of a contrast strength, a border strength, an edge strength, or a noise strength of a surface image of the engine component, wherein the inspection protocol can be saved and performed by the inspection processor.

6. The system of claim 1, further comprising an image library comprising a plurality of stored images, wherein the inspection processor is configured to access the image library and compare at least one of the surface images of the engine component to the plurality of stored images as a result of the automated inspection protocol.

7. The system of claim 1, wherein the inspection processor is configured to operate the illumination source, the imaging system, and the component manipulation system while performing the automated inspection protocol.

8. A method comprising:
developing an automated inspection protocol configured to acquire and analyze at least one surface image of an engine component, wherein developing the automated inspection protocol comprises
setting a plurality of inspection parameters for the automated inspection protocol, wherein the plurality of inspection parameters includes at least one of a contrast strength, a border strength, an edge strength, or a noise strength;
initiating the automated inspection protocol using a computer based user interface connected to an inspection processor; and
performing the automated inspection protocol using the inspection processor, wherein in preforming the automated inspection protocol comprises:
acquiring surface images of the engine component at a variety of positions using the inspection processor, wherein the inspection processor controls an illumination source, an imaging system, and an component manipulation system to acquire the surface images of the engine component, wherein the illumination source is configured to illuminate the engine component using visible light, wherein the imaging system is configured to capture the surface images of the engine component based on the illumination of the engine component using the visible light, and wherein the component manipulation system configured to position the engine component in the variety of orientations relative to at least one of the illumination source and the imaging system;
performing a fuzzy logic analysis on at least one of the surface images of the engine component to detect a defect on a surface of the engine component; and
reporting the defect to the computer based user interface.

9. The method of claim 8, wherein the developing the automated inspection protocol comprises selecting the automated inspection protocol from a predefined list of automated inspection protocols.

10. The method of claim 8, wherein setting a plurality of inspection parameters for the automated inspection protocol comprises applying a mask feature to a surface image of the engine component.

11. The method of claim 8, wherein reporting the defect to the computer based user interface comprises generating a report that describes the results of the automated inspection protocol.

12. The method of claim 11, wherein generating the report that describes the results of the automated inspection protocol further comprises determining at least one of a pass grade, a reject grade, and a repair grade for the engine component based on the defect.

13. The method of claim 8, wherein performing the automated inspection protocol using the inspection processor further comprises accessing an image library comprising a plurality of stored images and comparing at least one of the surface images of the engine component to the plurality of stored images as a result of the automated inspection protocol.

14. The system of claim 4, wherein the plurality of automated inspection protocols includes at least one of background removal, mask application, or edge detection.

* * * * *